United States Patent
Cannell et al.

(10) Patent No.: US 7,815,900 B1
(45) Date of Patent: Oct. 19, 2010

(54) USE OF C3-C5 MONOSACCHARIDES TO PROTECT KERATINOUS FIBERS

(75) Inventors: David W. Cannell, Plainfield, NJ (US); Natalya Fadeeva, Clark, NJ (US); Nghi Van Nguyen, Edison, NJ (US)

(73) Assignee: L'Oréal S.A., Paris (FR)

(*) Notice: Subject to any disclaimer, the term of this patent is extended or adjusted under 35 U.S.C. 154(b) by 0 days.

(21) Appl. No.: 09/614,118

(22) Filed: Jul. 11, 2000

(51) Int. Cl.
- *A61K 8/00* (2006.01)
- *A61K 8/72* (2006.01)
- *A61K 8/73* (2006.01)
- *A61Q 5/00* (2006.01)

(52) U.S. Cl. .................. 424/70.1; 424/70.9; 424/70.11; 424/70.13

(58) Field of Classification Search ................ 424/70.1, 424/70.11, 70.13, 70.9; 132/206, 211
See application file for complete search history.

(56) References Cited

U.S. PATENT DOCUMENTS

| | | | |
|---|---|---|---|
| 4,900,545 A * | 2/1990 | Wisotzki et al. | ......... 424/70.13 |
| 4,935,229 A * | 6/1990 | Naito et al. | |
| 4,971,080 A | 11/1990 | Rubenstein et al. | |
| 5,348,737 A | 9/1994 | Syed et al. | |
| 5,460,630 A | 10/1995 | Ouziel et al. | |
| 5,617,883 A * | 4/1997 | Savaides et al. | |
| 5,641,477 A * | 6/1997 | Syed et al. | |
| 5,660,838 A * | 8/1997 | Koga et al. | |
| 5,688,930 A | 11/1997 | Bertho et al. | |
| 5,866,111 A * | 2/1999 | Felardos et al. | |
| 5,888,951 A | 3/1999 | Gagnebien et al. | |
| 6,116,250 A * | 9/2000 | Buheitel | |
| 6,241,977 B1 * | 6/2001 | McMullen et al. | |
| 6,486,105 B1 | 11/2002 | Cannell et al. | |
| 6,495,147 B1 | 12/2002 | Dumas et al. | |
| 6,610,826 B1 | 8/2003 | Meyer et al. | |
| 6,638,519 B1 | 10/2003 | Lorant | |

FOREIGN PATENT DOCUMENTS

| | | |
|---|---|---|
| DE | 195 05 154 | 8/1996 |
| DE | 195 40 853 | 5/1997 |
| DE | 297 09 853 U1 | 10/1998 |
| DE | 19755800 A1 | 6/1999 |
| DE | 10036329 A1 | 2/2002 |

(Continued)

OTHER PUBLICATIONS

Milczarek et al., "The Mechanism and Stability of Thermal Transitions in Hair Keratin," *Colloid and Polymer Science*, vol. 270, 11, pp. 1106-1115 (1992).

(Continued)

*Primary Examiner*—Humera N Sheikh
(74) *Attorney, Agent, or Firm*—Finnegan, Henderson, Farabow, Garrett & Dunner, L.L.P.

(57) ABSTRACT

Methods of protecting keratinous fibers from extrinsic damage and/or repairing keratinous fibers damaged by extrinsic conditions by applying to keratinous fibers a composition comprising at least one sugar chosen from C3 to C5 monosaccharides and derivatives of these monosaccharides. Extrinsic damage is damage that is caused by conditions such as sun, chemical damage, e.g., from detergents, bleaching, relaxing, dyeing, and permanent waving, and heat, e.g., from hair dryers or curlers. Examples of keratinous fiber include hair, eyelashes, and eyebrows.

10 Claims, 1 Drawing Sheet

FOREIGN PATENT DOCUMENTS

| | | |
|---|---:|---|
| EP | 13736 | 8/1980 |
| JP | A 62 412 | 1/1987 |
| JP | 63243020 | 10/1988 |
| JP | A-63-258804 | 10/1988 |
| JP | A-03-148211 | 6/1991 |
| JP | A-04-036212 | 2/1992 |
| JP | 04266812 | 9/1992 |
| JP | 06122614 | 5/1994 |
| JP | 8040846 | 2/1996 |
| JP | 08143416 | 6/1996 |
| JP | A-08-151313 | 6/1996 |
| JP | 09059134 | 3/1997 |
| JP | 10279439 | 10/1998 |
| JP | A 10 306017 | 11/1998 |
| JP | 2001131015 | 5/2001 |
| JP | A 2001 131015 | 5/2001 |
| JP | A 2001 302470 | 10/2001 |
| JP | 2002508392 | 3/2002 |
| JP | A 2002 540128 | 11/2002 |
| WO | WO 95/09629 | 4/1995 |
| WO | WO 01/18096 | 3/2001 |

OTHER PUBLICATIONS

Hollenberg et al., "M öglichkeiten Zur Beeinflussung Der Haarstruktur Durch Pflegeprodukte," SÖFW-Journal, 121, 2, pp. 82-89 (1995).
ACS Abstract 123:296216 CA: Hollenberg et al., SÖ FW-Journal, 121, 2, pp. 82-89 (1995).
Hollenberg et al., "M öglichkeiten Zur Beeinflussung Der Haarstruktur Mit Kosmetischen Mitteln," Seifen—Öle—Fette—Wachse, 117, pp. 9-18 (1991).
ACS Abstract 114:149908 CA: Hollenberg et al.,Seifen—Öle—Fette—Wachse, 117, pp. 9-18 (1991).
Spei et al., "Thermoanalytical Investigations of Extended and Annealed Keratins," Colloid & Polymer Science, 265, pp. 9650-970 (1987).
Sandhu et al., "A Sim ple and Sensitiv e Technique, Based on Protein Loss M easurements, to Assess Surface Damage to Human Hair," J. Soc. Cosm et. Chem. vol. 44, pp. 163-175 (1993).
ACS Abstract (AN: 125:30893 CA): Chunhua Song et al., "Antimutagenic effect of vitamin B12 and glucose in cold waving agent (a hair conditioner),"Gongye Weisheng Yu Zhiyebing (1996), 22(1), 12-13.
ACS Abstract: J. Soc. Dyers Colour. (1995), 111(9), 293-7.
ACS Abstract (AN: 109:45463 CA): Tania Forst et al., "Modification of wool fibers during chemical treatment applied for dyeing optimization," Ind. Usoara: Text., Tricotaje, Confectii Text. (1987), 38(12), 560-2.
ACS Abstract (AN: 77:141244 CA): Yasuharu Fujiwara et al., "Amino-carbonyl reaction of wool," Sen'i Gakkaishi (1972), 28(4-5), 142-6.
Derwent Abstract of J03240730 (Oct. 28, 1991).
Derwent Abstract of J04273806 (Sep. 30, 1992).
Derwent Abstract of J05221823 (Aug. 31, 1993).
Derwent Abstract of U.S. Patent No. 5,349,737 (Sep. 20, 1994).
Derwent Abstract of J06287110 (Oct. 11, 1994).
Derwent Abstract of FR 2 704 751 (Nov. 10, 1994).
Derwent Abstract of J09077650.
Derwent Abstract of J09124453 (May 13, 1997).
Derwent Abstract of U.S. Patent No. 5,641,477 (Jun. 24, 1997).
Derwent Abstract of J10017430 (Jan. 20, 1998).
Abstract of WO 99/24009 (May 20, 1999).
Abstract of JP 08217656 (Aug. 27, 1996).
Abstract of JP 08151313 (Jun. 11, 1996).
Abstract of JP 040306212 (Mar. 13, 1992) and of US 5,660,838 (Aug. 26, 1997).
Abstract of U.S. Patent No. 4,900,545 (Feb. 13, 1990).
Abstract of DE 4109999 (Oct. 1, 1992).
Abstract of U.S. Patent No. 5,348,737 (Sep. 20, 1994).
Abstract of DE 4440315 (May 15, 1996).
Abstract of U.S. Patent Application 5,641,477 (Jun. 24, 1997).
Abstract of EP-750900 A1 (Jan. 2, 1997).
Abstract of DE 440315 (May 15, 1996).
Abstract of EP-829255 A2 (Mar. 18, 1998).
Abstract of DE 29709853 (Oct. 8, 1998).
Abstract of J10306017 (Nov. 17, 1998).
Abstract of J08217656 (Aug. 27, 1996).
Abstract of J07258041 (Oct. 9, 1995).
Abstract of J01213213 (Aug. 28, 1989).
Abstract of U.S. Patent Application 4,971,080 (Nov. 20, 1990).
Abstract of EP-469232 A (Feb. 5, 1992).
Abstract of J03148211 (Jun. 25, 1991).
Abstract of J02204407 (Aug. 14, 1990).
Abstract of DE 3820030 (Jul. 27, 1989).
Abstract of EP-398177 A (Nov. 22, 1990).
Abstract of EP-555086 A1 (Aug. 11, 1993).
Abstract of WO 93/23512 (Nov. 25, 1993).
Abstract of DE 4413434 (Oct. 19, 1995).
Swift, J. Alan, "Mechanism of split-end formation in human head hair", J. Soc. Cosmet. Chem., vol. 48, Mar./Apr. 1997, pp. 123-126.
David W. Cannell et al (Inventors) for Compositions Comprising at Least One Aminated C5-C7 Saccharide Unit, and Their Use for the Protection and/or Repair of Keratinous Fibers: Co-pending U.S. Appl. No. 09/820,954, filed Mar. 30, 2001.
David W. Cannell et al. (Inventors) for Heat Activated Durable Styling Compositions Comprising C3-C5 Monosaccharides and Methods for Same; Co-pending U.S. Appl. No. 09/821,480, filed Mar. 30, 2001.
David W. Cannell et al. (Inventors) for Compositions Comprising at Least One C1-C22 Substituted C3 to C5 Monosaccharide Unit, and Their Use for the Protection and/or Repair of Keratinous Fibers; Co-pending U.S. Appl. No. 09/820,812, filed Mar. 30, 2001.
David W. Cannell et al. (Inventors) for Heat Activated Durable Conditioning Compositions Comprising an Animated C3 to C5 Saccharide Unit and Methods for Using the Same; Co-pending U.S. Appl. No. 09/820,858, filed Mar. 30, 2001.
David W. Cannell et al. (Inventors) for Heat Activated Durable Styling Compositions Comprising C1 to C22 Substitutes C3-C5 Monosaccharides and Methods for Same; Co-pending U.S. Appl. No. 09/820,856, filed Mar. 30, 2001.
David W. Cannell et al. (Inventors) for Heat Activated Durable Conditioning Compositions Comprising C1 to C22 Substituted C3-C5 Monosaccharides and Methods for Using the Same; Co-pending U.S. Appl. No. 09/820,934, filed Mar. 30, 2001.
English Abstract for DE 195 05 154.
English Abstract for JP-A-04-036212.
English Abstract for JP-A-08-151313.
English Abstract for JP-A-63-258804.
English Abstract for JP-A-03-148211.
English Abstract for JP 63243020.
English Abstract for JP A 2002 540128.
English Abstract for JP A 2001 302470.
English Abstract for JP A 2001 131015.
English Abstract for JP A 10 306017.
English Abstract for JP A 62 412.
English Abstract for DE 195 40 853.
English-language Abstract of JP 8143416 A.
M. Feughelman, The Physical Properties of Alpha-Keratin Fibers, J. Soc'y Cosmetic Chem. 33, 385-406 (1982).
CTFA Int'l Cosmetic Ingredient Dictionary, 8th ed. p. 1744-47 (2000).
Trezl et al., Increase in Dye Pick-Up Wool Caused by the Maillard Reaction, J. Soc. Dyers Colour 111(9), 293-7 (1995).
Office Action dated Jun. 17, 2002 in previously co-pending U.S. Appl. No. 09/820,954 (now U.S. Patent No. 7,431,937).
Office Action dated Dec. 31, 2002 in previously co-pending U.S. Appl. No. 09/820,954 (now U.S. Patent No. 7,431,937).
Office Action dated Jul. 14, 2004 in previously co-pending U.S. Appl. No. 09/820,954 (now U.S. Patent No. 7,431,937).
Office Action dated Mar. 23, 2005 in previously co-pending U.S. Appl. No. 09/820,954 (now U.S. Patent No. 7,431,937).

BPAI Decision dated Mar. 13, 2008, Examiner Reversed, in previously co-pending U.S. Appl. No. 09/820,954 (now U.S. Patent No. 7,431,937).
Office Action dated Aug. 13, 2002 in previously co-pending U.S. Appl. No. 09/821,480.
Office Action dated Jan. 9, 2003 in previously co-pending U.S. Appl. No. 09/821,480.
Office Action dated May 21, 2003 in previously co-pending U.S. Appl. No. 09/821,480.
Office Action dated Feb. 6, 2004 in previously co-pending U.S. Appl. No. 09/821,480.
Office Action dated Sep. 22, 2004 in previously co-pending U.S. Appl. No. 09/821,480.
Office Action dated May 10, 2005 in previously co-pending U.S. Appl. No. 09/821,480.
Office Action dated Jan. 26, 2006 in previously co-pending U.S. Appl. No. 09/821,480.
Office Action dated May 21, 2002 in previously co-pending U.S. Appl. No. 09/820,812 (now U.S. Patent No. 7,201,894 ).
Office Action dated Oct. 23, 2002 in previously co-pending U.S. Appl. No. 09/820,812 (now U.S. Patent No. 7,201,894).
Office Action dated Feb. 9, 2004 in previously co-pending U.S. Appl. No. 09/820,812 (now U.S. Patent No. 7,201,894).
Office Action dated Jul. 28, 2004 in previously co-pending U.S. Appl. No. 09/820,812 (now U.S. Patent No. 7,201,894).
Office Action dated Aug. 11, 2005 in previously co-pending U.S. Appl. No. 09/820,812 (now U.S. Patent No. 7,201,894).
Office Action dated Apr. 10, 2006 in previously co-pending U.S. Appl. No. 09/820,812 (now U.S. Patent No. 7,201,894).
Office Action dated Aug. 27, 2002 in previously co-pending U.S. Appl. No. 09/820,858 (now U.S. Patent No. 7,459,150).
Office Action dated Jan. 17, 2003 in previously co-pending U.S. Appl. No. 09/820,858 (now U.S. Patent No. 7,459,150).
Office Action dated May 5, 2004 in previously co-pending U.S. Appl. No. 09/820,858 (now U.S. Patent No. 7,459,150).
Office Action dated Feb. 8, 2005 in previously co-pending U.S. Appl. No. 09/820,858 (now U.S. Patent No. 7,459,150).
Office Action dated Jul. 5, 2005 in previously co-pending U.S. Appl. No. 09/820,858 (now U.S. Patent No. 7,459,150) withdrawn by Pre-Appeals Conference Decision dated Nov. 18, 2005.
Office Action dated Feb. 17, 2006 in previously co-pending U.S. Appl. No. 09/820,858 (now U.S. Patent No. 7,459,150).
Office Action dated Aug. 25, 2006 in previously co-pending U.S. Appl. No. 09/820,858 (now U.S. Patent No. 7,459,150).
Office Action dated Nov. 24, 2006 in previously co-pending U.S. Appl. No. 09/820,858 (now U.S. Patent No. 7,459,150).
Bpai Decision dated Jul. 29, 2008, Examiner Reversed, in previously co-pending U.S. Appl. No. 09/820,858 (now U.S. Patent No. 7,459,150).
Office Action dated Jan. 29, 2003 in previously co-pending U.S. Appl. No. 09/820,856 (now U.S. Patent No. 6,800,302).
Office Action dated Jul. 29, 2003 in previously co-pending U.S. Appl. No. 09/820,856 (now U.S. Patent No. 6,800,302).
Office Action dated Aug. 13, 2002 in previously co-pending U.S. Appl. No. 09/820,856 (now U.S. Patent No. 6,800,302).
Office Action dated Dec. 23, 2002 in previously co-pending U.S. Appl. No. 09/820,856 (now U.S. Patent No. 6,800,302).
Office Action dated Jun. 24, 2003 in previously co-pending U.S. Appl. No. 09/820,856 (now U.S. Patent No. 6,800,302).
Office Action dated Sep. 22, 2004 in previously co-pending U.S. Appl. No. 09/820,856 (now U.S. Patent No. 6,800,302).
Office Action dated Apr. 18, 2005 in previously co-pending U.S. Appl. No. 09/820,934.
BPAI Decision dated Aug. 20, 2007, Examiner Affirmed, in previously co-pending U.S. Appl. No. 09/820,934.

* cited by examiner

USE OF C3-C5 MONOSACCHARIDES TO PROTECT KERATINOUS FIBERS

The present invention is directed to methods of treating keratinous fibers with a composition containing at least one sugar chosen from C3-C5 monosaccharides in order to provide protection from extrinsic damage. For example, the inventive methods can provide protection to keratinous fibers from heat, UV radiation, and chemical damage. More particularly, the present invention is directed to methods that provide protection benefits to keratinous fibers, including hair, eyelashes, and eyebrows, using compositions comprising C3-C5 monosaccharides.

Keratinous fibers, especially hair, are constantly exposed to harsh extrinsic conditions such as sun, chemical damage, e.g., from detergents, bleaching, relaxing, dyeing, and permanent waving, and heat, e.g., from hair dryers or curlers. These external factors generally result in damage to the keratinous fibers. More specifically, extrinsic conditions may disrupt the organized structure of the hair fibers, called the α-structure, which may be accompanied by a decrease in the tensile strength. The extrinsic damage to hair, as one would imagine, is more evident the further the hair fiber has grown from the root, because the hair has been exposed longer to the elements. In effect, the hair has what may be called a "damage history" as it grows, i.e., the further from the root, the lower the tensile strength and the greater the breakdown in α-structure that has occurred.

Morphologically, a hair fiber contains four structural units: cuticle, cortex, medulla, and intercellular cement. Robbins, C. R. *Chemical and Physical Behavior of Human Hair*, $3^{rd}$ Edition, Springer-Verlag (1994). The cuticle layers are located on the hair surface and consist of flat overlapping cells ("scales"). These scales are attached at the root end and point toward the distal (tip) end of the fiber and form layers around the hair cortex. The cortex comprises the major part of the hair fiber. The cortex consists of spindle-shaped cells, macrofibrils, that are aligned along the fiber axis. The macrofibrils further consist of microfibrils (highly organized protein units) that are embedded in the matrix of amorphous protein structure. The medulla is a porous region in the center of the fiber. The medulla is a common part of wool fibers but is found only in thicker human hair fibers. Finally, the intercellular cement is the material that binds the cells together, forming the major pathway for diffusion into the fibers.

The mechanical properties of the hair are determined by the cortex. A two-phase model for the cortex organization has been suggested. Milczarek et al, *Colloid Polym. Sci.*, 270, 1106-1115 (1992). In this model, water-impenetrable microfilaments ("rods") are oriented parallel with the fiber axis. The microfilaments are embedded in a water-penetrable matrix ("cement"). Within the microfilaments, coiled protein molecules are arranged in a specific and highly organized way, representing a degree of crystallinity in the hair fiber.

Similar to other crystalline structures, hair fibers display a distinct diffraction pattern when examined by wide-angle X-ray diffraction. In normal, non-stretched hair fibers this pattern is called an "alpha-pattern". The alpha-pattern or α-structure of hair is characterized by specific repeated spacings (9.8 Å, 5.1 Å, and 1.5 Å). All proteins that display this X-ray diffraction pattern are called α-proteins and include, among others, human hair and nails, wool, and porcupine quill. When the hair fiber is stretched in water, a new X-ray diffraction pattern emerges that is called a "β-pattern", with new spacings (9.8 Å, 4.65 Å, and 3.3 Å).

It is the α-structure of the cortex that is sensitive to hair damage by extrinsic conditions. When normal hair is damaged by heat, chemical treatment, or UV radiation, a decrease in the crystallinity or α-structure and a decrease in the disulfide bonds is observed. There is a need, therefore, for cosmetic products that are useful in protecting the α-structure of keratinous fibers from harsh extrinsic conditions and restoring the α-structure following damage by extrinsic conditions.

Such products are, for example, cosmetic compositions containing sugars. Sugars and sugar derivatives are one class of the countless number of compounds that have been added to hair care compositions in order to protect hair and improve desired properties of hair. As a result, the use of sugars and sugar derivatives in hair care compositions is well documented. A search of the literature uncovers the use of sugars in compositions for improving the quality of hair fibers, and preventing and repairing damage/stress to hair. The manifestations of improvements or preventive applications of sugars include less degradation of the hair, retained tensile strength, improved combability and reduced protein loss.

Documented uses of sugars in hair care compositions include: the use of glucose to improve the tactile and elastic properties of natural hair (Hollenberg and Mueller, *SOFW J.* 121(2) (1995)); the use of glucose for hair damage prophylaxis and damaged hair repair (Hollenberg & Matzik, *Seifen, Oele, Fette, Wachase* 117(1) (1991)); the use of glucose in shampoos (J04266812, assigned to Lion Corp.); the use of trehalose for moisture retention (J06122614, assigned to Shiseido Co. Ltd.); a composition for the lanthionization of hair comprising a sugar (U.S. Pat. Nos. 5,348,737 and 5,641,477, assigned to Avlon Ind. Inc.); the incorporation of xylobiose into cosmetic compositions to provide enhanced moisture retention and reduce excessive roughness and dryness of the skin and hair (U.S. Pat. No. 5,660,838, assigned to Suntory Ltd.); a composition for the regeneration of hair split-ends that contains at least one mono- or di-saccharide (U.S. Pat. No. 4,900,545, assigned to Henkel); hair care compositions to improve hair strength, hold and volume that contain C5 to C6 carbohydrates such as glucose; the use of fucose in a hair treatment to prevent split ends (DE29709853, assigned to Goldwell GMBH); and the use of saccharides in a shampoo to improve combing properties and control hair damage (J09059134, assigned to Mikuchi Sangyo KK).

In essence, all types of sugars have been applied to hair for countless reasons from moisturizing to enhancing hair growth (J10279439, assigned to Kureha Chem. Ind. Co. Ltd.). Clearly, however, not all sugars are the same and not all sugars impart the same properties when applied to a keratinous fiber. Additionally, the use of specific sugars that protect hair from extrinsic damage and, more particularly, protect the α-structure of hair from such damage has not been demonstrated. As a result, if sugars are going to be useful in protecting hair from extrinsic damage, a better understanding of the advantages of using sugars in hair care compositions is needed, and more specifically, an understanding of how sugars may be useful in restoring and protecting keratinous fibers.

To achieve at least one of these and other advantages, the present invention, in one aspect, provides a method of protecting keratinous fibers from extrinsic damage, e.g., disruption of the α-structure, protein loss, and/or denaturing caused by exposure to heat, chemicals, etc., by applying to keratinous fibers a composition that contains at least one sugar chosen from C3 to C5 monosaccharides and derivatives of these monosaccharides, where the sugar is present in an effective amount to protect the keratinous fibers. In the context of this invention, "protected" means that the keratinous fibers demonstrated a greater degree of preservation of the α-structure and the tensile strength. The composition may also contain at least one additional sugar.

The present invention is also drawn to a method of repairing keratinous fibers following extrinsic damage comprising applying to damaged keratinous fibers a composition comprising at least one sugar chosen from C3 to C5 monosaccharides and derivatives of these monosaccharides, where the sugar is present in an amount effective to repair the keratinous fibers. In the context of this invention, "repairing" means that the damaged keratinous fibers demonstrated an increase in α-structure and/or tensile strength following treatment of the damaged keratinous fibers with the compositions of the invention. The composition may also contain at least one additional sugar.

It is to be understood that both the foregoing general description and the following detailed description are exemplary and explanatory only and are not restrictive of the invention as claimed.

Figure 1:
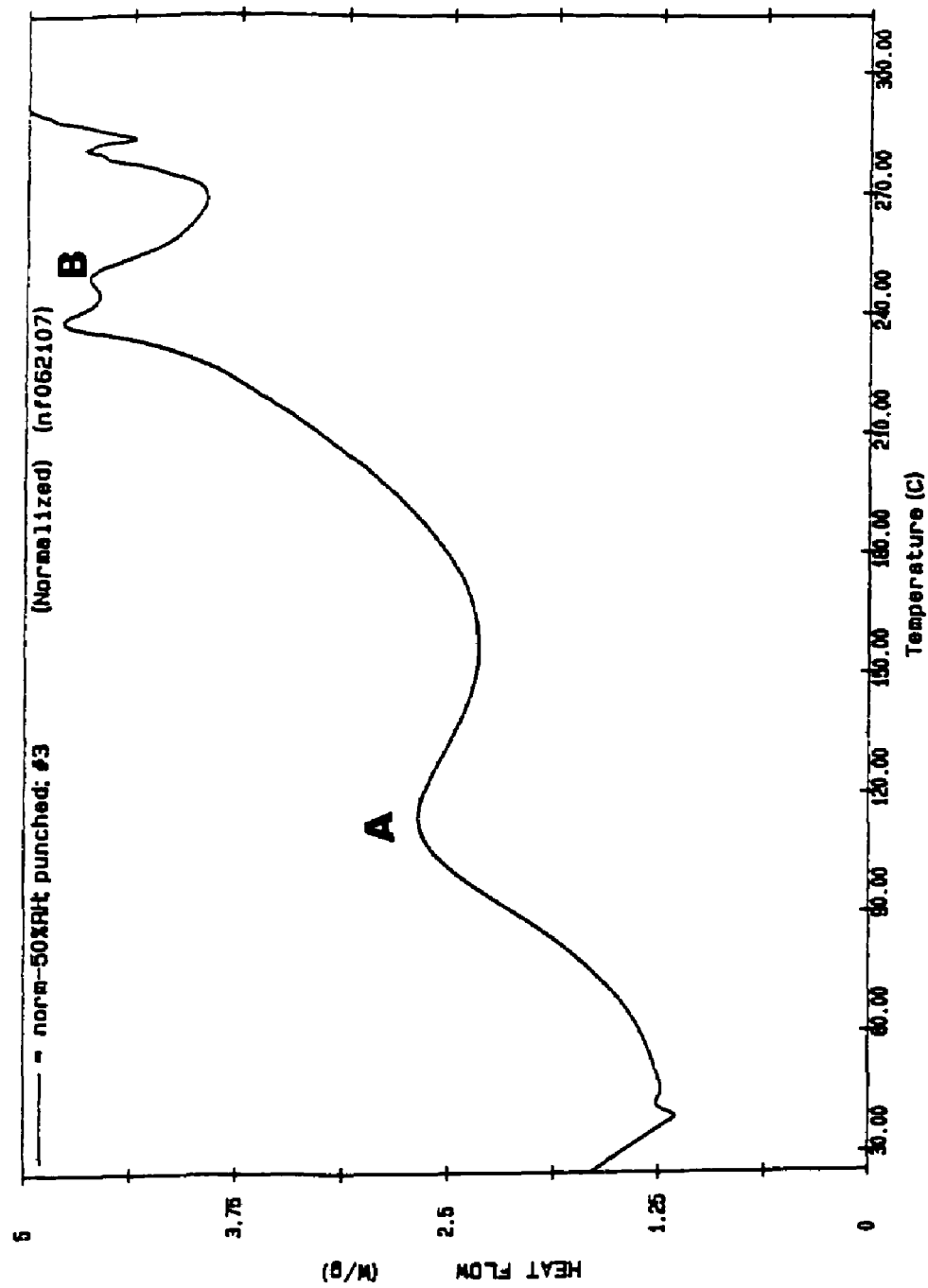
FIG. 1: A DSC (Differential Scanning Calorimetry) thermogram of normal brown hair. The hair sample was heated from 25° C. to 300° C. at a heating rate of 20° C./min. Peak A is the water release peak. Doublet peak B corresponds to the melting or rearrangement of the α-structure and its matrix contribution.

Reference will now be made in detail to exemplary embodiments of the present invention. The invention, in one aspect, provides methods of protecting keratinous fibers from extrinsic damage and/or repairing keratinous fibers damaged by extrinsic conditions by applying to keratinous fibers a composition that contains at least one sugar chosen from C3 to C5 monosaccharides and derivatives of these monosaccharides, wherein the at least one sugar is present in an amount effective to protect the keratinous fibers. The composition may also contain at least one additional sugar. Extrinsic damage is damage that is caused by one or more conditions such as sun, chemical damage, e.g., from detergents, bleaching, relaxing, dyeing, and permanent waving, and heat, e.g., from hair dryers or curlers. Examples of keratinous fiber include hair, eyelashes, and eyebrows.

As described above, sugars have been used extensively in hair care compositions and other treatments for their moisture retaining properties. However, it was unexpectedly discovered by the present inventors that, in addition to retaining moisture, a special class of sugars provided improved protection from at least one extrinsic condition to the keratinous fibers and also helped to restore damage caused by such extrinsic condition(s). More specifically, C3 to C5 monosaccharides were found to protect the α-structure of the hair cortex.

The inventors do not intend to be limited as to theory, but, as described above, the mechanical properties of the hair are determined by the cortex, where coiled protein molecules are arranged in a specific and highly organized pattern (the "α-structure"), representing a degree of crystallinity in the hair fiber. Because the α-structure is sensitive to extrinsic conditions, the extent of damage to the hair by extrinsic conditions can be monitored by monitoring changes in the α-structure.

In addition to X-ray diffraction, which allows one to determine the presence of a crystalline structure in the material, one may determine a relative amount of crystallinity in the material by employing a much simpler method called differential scanning calorimetry (DSC). DSC is based on the fact that all materials have an ability to absorb a certain amount of energy on heating, and this amount of energy is sensitive to changes in the structure, phase, and composition of the material. For example, the amount of energy a material absorbs may change when a material undergoes a change in crystal structure, a phase transition, such as melting, or the loss of water.

In DSC, a small sample of material is sealed in a cell and the material is heated at a steady rate. The power required to achieve a certain temperature in the sample is compared to the power required to achieve the same temperature in the empty cell, which serves as a reference. The difference in the amount of heat input between the reference and the sample is recorded as a function of temperature. In the absence of phase transitions in the sample, there is no change in heat input to maintain a constant temperature.

However, the amount of energy needed to maintain the temperature changes when the material undergoes a phase transition. For example, in a case where the material loses water, the water loss is an endothermic process, i.e., it requires energy. The sample will absorb more energy as compared to the reference in order for the sample to remain at the same temperature as the reference. This process will be registered as an increase in the heat flow above the baseline in the form of a peak. The more water contained in the sample, the greater the peak area.

For example, it is well known that water plays an important role in physico-chemical properties of the keratin fibers. The moisture content in dry fibers depends on both the relative humidity of the environment and on the condition of the hair. The water in the hair fiber can exist in three forms: 1) water adsorbed strongly on binding sites, 2) water adsorbed weakly on binding sites, and 3) loosely bound or free water. Based on the values for the heat of hydration found for each of the groups, it can be speculated that strongly bound binding sites include amino groups (hydration heat of 16.8 kcal/mole), while weakly bound binding sites may include hydroxyl and carboxylic groups (5.7 kcal/mole and 7.4 kcal/mole, respectively).

Using DSC, one can observe the loss of water due to exposure of the hair to heat. The loosely bound and free water should be removed around 100° C., while the release of the strongly bound water should be observed above 140° C. In the DSC of keratinous fibers, a broad endotherm is observed from 75° C. to 200° C., which is initially related to removal of the free water, and then to the removal of more strongly bound water (FIG. 1).

In a similar way, if a melting process or any other change in the crystal structure takes place in the sample, it requires additional energy, and thus will be manifested in the form of a peak on the DSC curve. The greater the degree of crystallinity or organized structure in the sample, the greater the peak area that will be observed. Therefore, DSC is also an excellent tool for observing the change in the α-structure of keratinous fibers and is therefore sensitive to hair damage.

From 20% to 30% of the hair cortex occurs in a highly organized (α-helical) form. When the hair is heated above 230° C., a doublet peak is usually observed in DSC, which has been interpreted in terms of a first peak corresponding to the helix melting points (microfibrillar origin) and a second peak corresponding to cystine decomposition (matrix origin). Spei and Holzem, *Colloid & Polymer Sci.* 265, 965-970 (1987). However, further studies have shown that the first peak of the doublet, the microfibrillar peak, is more specifically a helix unfolding, superimposed by various decomposition reactions. Id. Herein, the term α-structure is associated with the doublet peak or peak area though technically the doublet area includes both a crystalline (microfibrillar) and non-crystalline (matrix) contribution. The α-structure represents the overall integrity of the fiber in an unstressed state. (See FIG. 1).

The greater the peak area, usually expressed in Joules per gram of hair, the higher the percentage of the hair cortex in the α-structure form. The DSC peak, at 210-250° C., also coincides with the disappearance of the alpha-pattern in the X-ray diffraction. Sandhu and Robbins, *J. Soc. Cosmet. Chem.*, 44, 163-175 (1993). In other words, when normal hair is damaged by heat, chemical treatment, or UV irradiation, a decrease in the doublet peak area of the DSC is observed and the amount of damage can be quantified by the peak area. The correlation between a decrease in DSC peak area and damage to the hair fibers is further verified by a corresponding decrease in the number of disulfide bonds (expressed as half-cystine) in the hair (see Table 1 below). A decrease in the number of disulfide bonds corresponds to a breakdown in the chemical structure of the hair.

TABLE 1

Effect of Chemical Treatment, Heat, and UV Irradiation on Chemical and Physical Properties of the Hair

| Hair type | Doublet peak area J/g hair | Half-Cystine micromole/g hair |
|---|---|---|
| Normal blonde hair | 81.57 +/− 8.28 | 918.7 +/− 165.8 |
| Blonde hair after: | | |
| Perm | 54.63 +/− 25.78 | 810.1 +/− 135.9 |
| Bleach | 53.22 +/− 13.12 | 740.1 +/− 45.9 |
| UV (180 h) | 13.98 +/− 11.78 | 629.7 +/− 8.8 |
| Heat (12 cycles at 130° C.)* | 18.63 +/− 8.56 | 654.3 +/− 50.7 |

*12 cycles, 1 min each, at 130° C.

The detrimental changes in the chemical composition and in the amount of the hair crystallinity are also accompanied by cuticle loss and/or a decrease in the tensile strength. Shown in Table 2 below is the correlation between the doublet peak area and the wet tensile strength of normal and damaged hair. The wet tensile strength is expressed as the work required to stretch the wet fiber to 25% of its original length.

TABLE 2

Correlation between the Doublet Peak Area and the Wet Tensile Strength of Normal and Damaged Hair

| Hair type | Doublet Peak Area J/g hair n = 5 DSC tests | Work 25% J/m² n = 100 fibers |
|---|---|---|
| Normal blonde hair | 25.00 +/− 4.90 | 555.0 +/− 122 |
| Blond hair after: | | |
| 12 heat cycles | 8.39 +/− 0.72 | 370 +/− 138 |
| Bleach | 6.90 +/− 0.55 | 222 +/− 93 |

The above demonstrates that damage to the hair involves a decrease in the percentage of the hair cortex in the α-structure form. The inventors have found, however, that the damage to the α-structure can be prevented or at least lessened if the hair is treated with solutions of C3-C5 monosaccharides (Nomenclature: C3-triose, C4-tetrose, C5-pentose, C6-hexose). Hexoses and other large monosaccharides do not appear to provide similar protection to the hair.

C3-C5 monosaccharides may also reduce cuticle loss and/or facilitate repair or re-building of the α-structure of the fibers following damage from extrinsic conditions. Although the inventors do not intend to be limited as to theory, the ability of a C3 to C5 monosaccharide to repair keratinous fibers may be due to a reaction between the hair and the C3 to C5 monosaccharide. When hair was treated with C3 to C5 monosaccharide solutions prior to heat application, changes in the chemical composition of the hair were observed. More specifically, the amount of lysine and arginine decreased, indicating what appears to be a Schiff base reaction between the aldehyde groups of the monosaccharides and the amine groups of the hair fibers.

Any triose, tetrose, or pentose may be useful in the practice of the invention. Exemplary C3 to C5 monosaccharides include, but are not limited to, aldopentoses such as xylose, arabinose, lyxose, and ribose; ketopentoses such as ribulose, and xylulose; aldotetroses such as erythrose, and treose; ketotetroses such as erythrulose; aldotrioses such as glyceraldehyde; and ketotrioses such as dihydroxyacetone. These exemplary compounds include C3 to C5 monosaccharides containing aldehyde groups (aldoses), furanoses and other ring structures.

Derivatives of C3 to C5 monosaccharides are also useful in the compositions and methods of the invention. Exemplary derivatives include, but are not limited to, amine derivatives such as lyxozylimine. For example, ammonias or primary amines may react with the aldehyde or ketone group of a sugar to form an imine, which is a compound containing the functional group C=N. These imine compounds are sometimes also referred to as Schiff bases. Other exemplary derivatives of C3 to C5 monosaccharides include, but are not limited to, hemiacetal, hemiketal or any oxidized derivatives. These derivatives may be formed by the reaction of the aldehyde or ketone group of a sugar with an alcohol. Still other exemplary derivatives of a C3 to C5 monosaccharide may also include, but are not limited to, dimers and oligomers of C3 to C5 monosaccharides such as xylobiose.

The compositions of the present invention may also contain at least one additional sugar which may aid in moisture retention. The effectiveness of a sugar in aiding in moisture retention may be measured by monitoring the DSC peak at a temperature ranging from 75° C. to 200° C. Compositions comprising mixtures of C3 to C5 monosaccharides are within the practice of the invention, as are compositions comprising mixtures of at least one C3 to C5 monosaccharide and at least one additional sugar.

The additional sugars useful in the present invention may be any sugar, carbohydrate or carbohydrate moiety. Exemplary additional sugars may be chosen from monosaccharides, which include, but are not limited to, any three to seven carbon sugars such as pentoses, e.g., ribose, arabinose, xylose, lyxose, ribulose, and xylulose, and hexoses, e.g., allose, altrose, glucose, mannose, gulose, idose, galactose, talose, sorbose, psicose, fructose, and tagatose; disaccharides (which are saccharides that hydrolyze into two monosaccharides) such as maltose, sucrose, cellobiose, trehalose and lactose; and polysaccharides (which are saccharides that hydrolyze into more than two monosaccharides) such as starch, dextrins, cellulose and glycogen. In another embodiment, the additional sugars of the invention are chosen from any aldoses or ketoses.

In one embodiment of the invention, a C3-C5 monosaccharide or a mixture of C3-C5 monosaccharides is present in the compositions of the present invention in an amount ranging from 0.01% to 5.00% relative to the total weight of the composition and more preferably in an amount ranging from 0.10% to 1.00%. When an additional sugar or mixture of additional sugars is present in the compositions of the present invention, it is preferably present in an amount ranging from 0.01% to 5.00% relative to the total weight of the composition and even preferably in an amount ranging from 0.10% to 1.00%.

The compositions used in the methods of the present invention may be in the form of a liquid, oil, paste, stick, spray, dispersion, emulsion, lotion, gel, or cream. The compositions of the present invention may also be provided as one-part compositions comprising at least one C3-C5 monosaccharide and, optionally, an additional sugar or mixture of additional sugars or in the form of a multi-component treatment or kit. The skilled artisan, based on the stability of the composition and the application envisaged, will be able to determine how the composition and/or multicomponent compositions should be stored and mixed. For example, simple sugars such as C3-C5 monosaccharides are known to be stable at pH levels ranging from 4 to 9. In compositions where the pH range is below or above these levels, the sugars would be stored separately and added to the composition only at the time of application.

The invention will be illustrated by, but is not intended to be limited to, the following examples.

EXAMPLES

Example 1

Effect of UV/Thermal History on the Structure of "Virgin" (Chemically Non-Treated) Hair A swatch of Caucasian hair, dark blonde, coarse and wavy, 5 inches long and cut from the root, was tested. The hair had never been treated in any way that would cause changes in its chemical composition such as perming, relaxing, or coloring. The hair had only been subject to shampoo, conditioner (including oil treatment), styling aids, and blow drying, as well as the normal conditions of nature.

The swatch was divided into two sections, each 2.5 inches in length. For the DSC experiments, the finely cut hair was accurately taken from the following parts of the swatch:

the extreme root end
the 2.5 inch length, and
the 5.0 inch length.

In the DSC experiments (using DSC-6 with Autosampler, Perkin Elmer) the hair was sealed in 40 ml pans with a 50 micron laser-drilled opening in the pan lid and was heated from 25° C. to 300° C. at a heating rate of 20° C./min. Three runs per section were performed. The results were averaged and standard deviations determined.

The two sections were also tested for wet tensile strength using the fiber tensile testing instrument Dia-Stron (50 fibers per test). The following parameters were determined: Young's Modulus (the spring constant, measured in $N/m^2$); Work to stretch the hair fiber 25% of its length ($J/m^2$); Extension to Break (how far hair can be stretched before breaking, measured in % of hair length); Work to Break ($J/m^2$).

The DSC results are presented in Table 3, and the Dia-Stron data in Table 4. In both tables, the extreme root part of the hair is taken as the zero point. These results show the intrinsic loss of α-structure in hair due to normal conditions.

TABLE 3

Alpha-structure of Normal Hair as a Function of the Hair Length

| Hair Length, inches | Doublet Peak Area, J/g hair |
| --- | --- |
| 0 | 37.75 +/− 5.91 |
| 2.5 | 27.28 +/− 10.70 |
| 5.0 | 21.36 +/− 7.36 |

TABLE 4

Wet Tensile Strength of Normal Hair as a Function of the Hair Length

| Hair Length, inches | Young's Modulus, $MN/m^2$ | Work 25% $J/m^2$ | Break % | Work to Break $J/m^2$ |
| --- | --- | --- | --- | --- |
| 0 to 2.5 | 732 +/− 114 | 395 +/− 103 | 60.3 +/− 4.3 | 1690 +/− 442 |
| 2.5 to 5.0 | 613 +/− 116 | 230 +/− 49 | 58.8 +/− 8.6 | 1100 +/− 232 |

Example 2

Effects of Monosaccharides on α-Structure and Tensile Strength of Bleached Hair

Normal blonde hair was bleached with Clairol Basic White Bleach (40 volume $H_2O_2$) for 20 min at standard room temperature and humidity. The bleached swatches were rinsed with tap water, and soaked in an excess of deionized water for 2 hours. The swatches were air-dried and equilibrated for 48 hours prior to further treatment. Some of the bleached swatches were subsequently "permed" using a Reforming Lotion (10% TGA, pH 8.8, 20 minutes) and then neutralized with 2% $H_2O_2$, pH 3 (5 minutes). The bleached/permed swatches were rinsed with tap water, and soaked in an excess of deionized water for 2 hours. The swatches were air-dried and equilibrated for 48 hours prior to further treatment. The swatches that were heat treated were treated with 0.06M solutions of hexoses and pentoses for 10 min at 45° C. and then were heated for 12 cycles. The swatches were rinsed after the heat application.

Tensile strength was determined using both the Instron (50 dry fibers per tests) and the Dia-Stron (100 wet fibers per test), with the stretching rate of 100 mm/min. The following parameters were determined: Young's Modulus ($N/m^2$), Work to stretch 25% ($J/m^2$); Extension to Break (degree of elongation) (%); Work to Break ($J/m^2$).

Differential Scanning Calorimetry

In the DSC tests, finely cut hair (4-5 mg) was crimped in an aluminum pan that was punctured prior to each run. The samples were heated from 25° C. to 300° C., at a scanning rate of 20° C./min, with 5 runs per treatment. The results were averaged.

The DSC data for the normal blonde hair before and after 12 heat cycles with water and 1% D-xylose in water, respectively, are shown in Table 5. The hair was normalized by sample size. The D-xylose solution appeared to protect the hair structure as compared to water.

TABLE 5

Effect of Heat Treatment on Thermal Properties of Normal Blonde Hair

| Treatment | Normalized area - J/g hair |
|---|---|
| Normal blonde hair, no heat treatment | 19.62 +/− 11.57 |
| Blonde hair after 12 heat cycles with: | |
| a. water | 8.17 +/− 2.62 |
| b. 1% D-Xylose in water | 16.05 +/− 5.05 |

When the bleached and the bleached/permed hair, respectively, underwent 12 heat cycles with solutions of pentoses and hexoses, the protection effect was found only for the pentoses, i.e., 1% D-xylose and 0.9% 2-deoxy-D-ribose (Table 6 and Table 7). In other words, the normalized α-structure peak area was larger for the hair treated with pentoses, indicating that significantly more of the α-structure remained undamaged in the hair treated with the pentoses.

TABLE 6

Effect of Monosaccharides (0.06 M) in Heat Treatment on Thermal Properties of Bleached Hair

| Treatment | Normalized area - J/g hair |
|---|---|
| Normal blonde hair, no heat treatment | 5.78 +/− 1.94 |
| Blonde hair after 12 heat cycles with: | |
| a. water | 5.78 +/− 1.94 |
| PENTOSES (inventive) | |
| b. 1% D-Xylose | 9.74 +/− 2.13 |
| c. 0.9% 2-Deoxy-D-ribose | 9.63 +/− 2.87 |
| HEXOSES (comparative) | |
| d. 1.1% L-Fucose | 5.26 +/ 1.59 |
| e. 1.2% D-Glucose | 5.76 +/ 1.16 |
| f. 1.2% D-Galactose | 5.39 +/ 2.29 |
| g. 1.2% D-Mannose | 5.47 +/ 1.27 |
| h. 1.2% D-Fructose | 6.51 +/ 1.71 |

TABLE 7

Effect of Monosaccharides (0.06 M) in Heat Treatment on Thermal Properties of Bleached/Permed Hair

| Treatment | Normalized area - J/g hair |
|---|---|
| Normal blonde hair, no heat treatment | 6.28 +/− 1.95 |
| Blonde hair after 12 heat cycles with: | |
| a. water | 4.73 +/− 0.87 |
| PENTOSES (inventive) | |
| b. 1% D-Xylose | 9.78 +/− 1.48 |
| c. 0.9% 2-Deoxy-D-ribose | 6.43 +/− 1.87 |
| HEXOSES (comparative) | |
| d. 1.1% L-Fucose | 4.85 +/ 1.25 |
| e. 1.2% D-Glucose | 4.96 +/ 0.32 |
| f. 1.2% D-Galactose | 4.91 +/ 0.71 |
| g. 1.2% D-Mannose | 3.98 +/ 1.26 |
| h. 1.2% D-Fructose | 4.70 +/ 1.15 |

Tensile Strength

The tensile properties using dry bleached hair before and after 12 heat cycles were determined using the Instron and is shown in Table 8. As with the DSC results, only the pentoses (treatments b and c) appeared to provide protection against heat. The Young's modulus values found for the bleached hair heated in the presence of the pentoses were noticeably different from the Young's modulus of the hair treated with water. On the other hand, there was no statistical difference between the water treatment and the hexose treatments.

TABLE 8

Effect of Monosaccharides (0.06 M) in Heat Treatment on Tensile Strength of Dry Bleached Hair (measured using the INSTRON) (n = 50 fibers)

| Treatment | Young's Modulus $MN/m^2$ | Work 25% $J/m^2$ | Extension-Break % | Work-Break $J/m^2$ |
|---|---|---|---|---|
| Normal blonde hair | 5,044 +/− 8.79 | 1,011 +/− 173 | 55.56 +/− 6.28 | 2,865 +/− 562 |
| Bleached hair | 4,751 +/− 914 | 875.1 +/− 153.6 | 57.82 +/− 7.06 | 2,599 +/− 624 |
| Blonde hair after 12 heat cycles with: | | | | |
| a. water | 4,496 +/− 875 | 858.6 +/− 147.5 | 59.68 +/− 5.64 | 2,521 +/− 499 |
| PENTOSES | | | | |
| b. 1% D-Xylose | 5,802 +/− 1,161 | 1,204 +/− 215 | 55.28 +/− 7.08 | 3,161 +/− 771 |
| c. 0.9% 2-Deoxy-D-ribose | 5,111 +/− 871 | 1,032 +/− 163 | 55.35 +/− 7.52 | 2,872 +/− 709 |
| HEXOSES | | | | |
| d. 1.1% L-Fucose | 4,331 +/− 860 | 838.2 +/− 134.5 | 57.01 +/− 6.18 | 2,346 +/− 543 |
| e. 1.2% D-Glucose | 4,623 +/− 813 | 913.9 +/− 158.2 | 56.01 +/− 7.21 | 2,599 +/− 604 |
| f. 1.2% D-Galactose | 4,724 +/− 913 | 945.8 +/− 168.9 | 58.82 +/− 6.21 | 2,696 +/− 533 |
| g. 1.2% D-Mannose | 4,746 +/− 688 | 914.9 +/− 122 | 57.33 +/− 5.98 | 2,595 +/− 433 |
| h. 1.2% D-Fructose | 4,492 +/− 852 | 885 +/− 161 | 59.89 +/− 8.11 | 2,644 +/− 644 |

The tensile properties of the wet bleached and bleached/permed hair before and after 12 heat cycles was determined using the Dia-Stron and are shown in Table 9. As was the case with the DSC results, the 1% xylose (C5, inventive) solution appeared to provide statistically significant protection against heat, as compared to water and the 1.2% D-glucose (C6, non-inventive) solution.

The treatment solutions included four pentoses (D-xylose, D-arabinose, D-lyxose, and D-ribose, 1% each) and one hexose (1.2% D-glucose). Deionized water was used as a control treatment. After the heat experiment, the hair was rinsed in water, air-dried, and equilibrated for 24 hours in the humidity chamber at 25° C. and 50% RH prior to further testing. These swatches are referred to as treated at 130° C.

TABLE 9

Effect of 1% Xylose (0.06 M) in Heat Treatment on Tensile Strength of Wet Bleached and Bleached/Permed Hair (DIA-STRON) n = 100 fibers

| Treatment | Young's Modulus $MN/m^2$ | Work 25% $J/m^2$ | Extension-Break % | Work-Break $J/m^2$ |
|---|---|---|---|---|
| 1. Normal blonde hair | 644.0 +/− 118.0 | 401.0 +/− 199.0 | 57.60 +/− 10.20 | 1,950 +/− 965 |
| 2. Bleached hair | 425.0 +/− 118.0 | 220.0 +/− 91.2 | 64.40 +/− 8.22 | 1,860 +/− 762 |
| 3. Blonde hair after 12 heat cycles with: | | | | |
| a.   water | 414.0 +/− 129.0 | 238.0 +/− 93.1 | 58.60 +/− 7.33 | 1,200 +/− 469 |
| b.   1% D-Xylose | 434.0 +/− 99.1 | 432.0 +/− 137.0 | 52.80 +/− 9.29 | 1,600 +/− 526 |
| c.   1.2% D-Glucose | 397.0 +/− 106.0 | 187.0 +/− 74.8 | 64.20 +/− 10.4 | 1,130 +/− 453 |
| 4. Bleached/permed hair | 201.0 +/− 135.0 | 88.3 +/− 34.4 | 65.50 +/− 7.75 | 558.0 +/− 218.0 |
| 5. Bleached/permed hair after 12 heat cycles with: | | | | |
| a.   water | 142.0 +/− 66.4 | 105.0 +/− 37.1 | 62.00 +/− 6.15 | 586.0 +/− 208.0 |
| b.   1% D-Xylose | 170.0 +/− 88.6 | 199.0 +/− 74.2 | 54.30 +/− 4.70 | 620.0 +/− 231.0 |
| c.   1.2% D-Glucose | 136.0 +/− 92.5 | 155.0 +/− 47.5 | 63.50 +/− 7.65 | 979.0 +/− 300 |

Based on the tensile properties and the DSC results, pentoses appear to provide protection against heat treatment, while little or no protection is provided by glucose.

Example 3

Thermal Protection after 5 Cycles at 45° C. and 130° C.: Pentoses vs. Hexoses

Normal blonde hair was bleached with Clairol Basic White Bleach, 40 volume $H_2O_2$, for 20 min at room temperature. One batch of normal and bleached hair swatches underwent five heat cycles at 130° C., where one treatment cycle involved the following steps (1-4):

1. The swatches were treated with 0.06 M solutions of monosaccharides in deionized water (about 1 wt %) for 10 min at 45° C.
2. The treated swatches were blow-dried for 1 min.
3. The heat was applied for 1 min in the form of a flat hair iron Windmere "Solid Gold" (130° C.).
4. The swatches were rinsed and blot-dried with a paper-towel.

A second batch of normal and bleached hair swatches were treated in a similar way and blow-dried, without application of the hot iron. The treatment was also repeated 5 times, the swatches from the second batch are referred to as treated at 45° C.

As shown in Table 10, even the relatively mild blow-drying treatment resulted in a decrease in the doublet-peak area, both on the normal and the bleached hair, while the addition of the hot iron treatment caused a further decrease, particularly pronounced in the normal hair. The pentose solutions resulted in the protection of the hair, while the hexose solution did not demonstrate the protection effect.

The dry tensile strength of the hair treated at 45° C. (Table 11) and at 130° C. (Table 12) was also protected by the pentoses but not by the hexose (D-glucose). It should be noted that three pentoses (D-xylose, D-arabinose, and D-ribose) seemed to provide improved protection both at 45° C. and at 130° C., while the fourth pentose, D-lyxose, provided better improved protection at 45° C.

TABLE 10

Decrease in the Doublet Peak Areas as a Result of Five Thermal Cycles: 45° C. vs. 130° C. (n = 5 DSC runs)

| Hair type | Doublet Peak Area, normalized, No heat | J/g hair 45° C. (blow drying) | 130° C. (blow-drying + hot iron) |
|---|---|---|---|
| Normal blonde hair after 5 cycles with: | 25.00 +/− 4.90 | | |
| deionized water | | 15.98 +/− 3.11 | 8.39 +/− 0.72 |
| 1.2% D-Glucose (hexose) | | 11.65 +/− 4.98 | 7.60 +/− 1.01 |
| 1.0% D-Xylose (pentose) | | 20.17 +/− 11.98 | 15.27 +/− 5.14 |

TABLE 10-continued

Decrease in the Doublet Peak Areas as a Result of Five Thermal Cycles: 45° C. vs. 130° C. (n = 5 DSC runs)

| Hair type | Doublet Peak Area, normalized, No heat | J/g hair 45° C. (blow drying) | 130° C. (blow-drying + hot iron) |
|---|---|---|---|
| Bleached hair after 5 cycles with: | 6.94 +/− 0.55 | | |
| deionized water | | 6.39 +/− 2.71 | 6.14 +/− 1.06 |
| hexose: | | | |
| 1.2% D-Glucose | | 6.35 +/− 2.71 | 5.37 +/− 1.22 |
| pentoses: | | | |
| 1.0% D-Xylose | | 8.41 +/− 1.33 | 9.66 +/− 2.59 |
| 1.0% D-Arabinose | | 7.78 +/− 1.07 | 8.22 +/− 0.90 |
| 1.0% D-Lyxose | | 8.26 +/− 3.02 | 6.23 +/− 0.59 |
| 1.0% D-Ribose | | 7.80 +/− 1.87 | 9.27 +/− 2.81 |

TABLE 11

Doublet Peak Area and Dry Tensile Strength of the Normal and the Bleached Hair after Five Heat Cycles at 45° C.: Effect of Treatments (0.06 M solutions)

| Hair type | Doublet Peak Area J/g hair n = 5 DSC tests | Work 25% J/m$^2$ n = 50 fibers |
|---|---|---|
| Normal blonde hair after 5 cycles at 45° C. with: | 25.00 +/− 4.90 | 1,011 +/− 173 |
| deionized water | 15.98 +/− 3.11 | 801.5 +/− 166.3 |
| 1.2% D-Glucose (hexose) | 11.65 +/− 4.98 | 837.0 +/− 255.9 |
| 1.0% D-Xylose | 20.17 +/− 11.98 | 1,155 +/− 224 |
| Bleached hair after 5 cycles at 45° C. with: | 6.94 +/− 0.55 | 875.1 +/− 153.6 |
| deionized water | 6.39 +/− 2.71 | 928.4 +/− 148.7 |
| hexose: | | |
| 1.2% D-Glucose | 6.35 +/− 2.71 | 984.6 +/− 169.6 |
| pentoses: | | |
| 1.0% D-Xylose | 8.41 +/− 1.33 | 1,182 +/− 215 |
| 1.0% D-Arabinose | 7.78 +/− 1.07 | 1,147 +/− 191 |
| 1.0% D-Ribose | 7.80 +/− 1.87 | 1,237 +/− 204 |
| 1.0% D-Lyxose | 8.26 +/− 3.02 | 1,157 +/− 228 |

TABLE 12

Doublet Peak Area and Dry Tensile Strength of the Normal and the Bleached Hair after Five Heat Cycles at 130° C.: Effect of Treatments (0.06 M solutions)

| Hair type | Doublet Peak Area J/g hair n = 5 DSC runs | Work 25% (Dry) J/m$^2$ n = 50 fibers |
|---|---|---|
| Normal blonde hair after 5 cycles with: | 25.00 +/− 4.90 | 1,011 +/− 173 |
| deionized water | 8.39 +/− 0.72 | 858.4 +/− 142.2 |
| hexose: | | |
| 1.2% D-Glucose | 7.60 +/− 1.01 | 836.9 +/− 119.6 |
| pentoses: | | |
| 1.0% D-Xylose | 15.27 +/− 5.14 | 1,150 +/− 818 |
| 1.0% D-Arabinose | 11.33 +/− 2.30 | 1,060 +/− 180 |
| 1.0% D-Lyxose | 8.35 +/− 0.81 | 883.4 +/− 174.2 |
| Bleached hair after 5 cycles with: | 6.94 +/− 0.55 | 875.1 +/− 153.6 |
| deionized water | 6.14 +/− 1.06 | 906.6 +/− 164.5 |
| hexose: | | |
| 1.2% D-Glucose | 5.37 +/− 1.22 | 864.7 +/− 184.4 |
| pentoses: | | |
| 1.0% D-Xylose | 9.66 +/− 2.59 | 1,051 +/− 191 |
| 1.0% D-Arabinose | 8.22 +/− 0.90 | 1,055 +/ 193 |
| 1.0% D-Ribose | 9.27 +/− 2.81 | 1,064 +/− 171.1 |
| 1.0% D-Lyxose | 6.23 +/− 0.59 | 819.9 +/− 162.7 |

Example 4

Thermal Protection after 12 Cycles at 130° C.: Pentoses vs. Hexoses

Normal blonde hair was divided in two batches. The hair from the first batch was bleached with Clairol Basic White Bleach, 40 volume $H_2O_2$, for 20 min at room temperature and humidity. The hair from the second batch was first bleached as above, and then permed: Reforming lotion-10% Thioglycolic acid, pH 8.8, 20 min; neutralizer-2% hydrogen peroxide, 5 min. The oxidatively damaged hair was equilibrated for 24 hours prior to further testing.

Both the bleached and the bleached/permed hair were subjected to heat treatment, as in Example 2. The heat treatment experiment involved 12 heat cycles including application of sugar or control solution before each heat application, and rinsing after the heat application. Deionized water was used as a control treatment.

After the heat experiment, the hair was rinsed in water, air-dried, and equilibrated for 24 h in the humidity chamber at 25° C. and 50% RH prior to further testing. The effect of the hexoses vs. pentoses on the dry tensile strength (INSTRON) and the alpha-structure (doublet peak area, DSC) was tested on the bleached hair (Table 13). The effect of a hexose (D-glucose) vs. a pentose (D-Xylose) on wet tensile strength (DIASTRON) was tested both on the bleached and the bleached/permed hair (Table 14). Application of 0.06M solutions of pentoses protected the bleached and the bleached/permed hair against thermal damage (α-structure; wet and dry tensile strength).

TABLE 13

Doublet Peak Area and Dry Tensile Strength of the Bleached Hair after 12 Heat Cycles: Effect of Treatments (0.06 M solutions)

| Hair type | Doublet Peak Area J/g hair n = 5 DSC runs | Work 25% (Dry) J/m² n = 100 fibers |
|---|---|---|
| Normal blonde hair | 19.62 +/− 11.57 | 1,011 +/− 173 |
| Bleached hair | 5.78 +/− 1.94 | 875.1 +/− 153.6 |
| Bleached hair after 12 heat cycles with: | | |
| deionized water | 5.76 +/− 1.94 | 875.1 +/− 153.6 |
| Hexoses: | | |
| D-Glucose | 5.56 +/− 1.16 | 913.9 +/− 158.2 |
| D-Galactose | 5.39 +/− 2.29 | 945.8 +/− 168.9 |
| D-Mannose | 5.47 +/− 1.27 | 914.9 +/− 122.0 |
| D-Fructose | 6.51 +/− 1.71 | 885.0 +/− 161.0 |
| L-Fucose | 5.26 +/− 1.59 | 838.2 +/− 134.5 |
| Pentoses: | | |
| D-Xylose | 9.74 +/− 2.13 | 1,204 +/− 215 |
| 2-Deoxy-D-ribose | 9.63 +/− 2.87 | 1,032 +/− 163 |

TABLE 14

Doublet Peak Area and Wet Tensile Strength of the Bleached/Permed Hair after 12 Heat Cycles: Effect of Treatments (0.06 M solutions)

| Hair type | Doublet Peak Area J/g hair n = 5 DSC runs | Work 25% (Wet) J/m² n = 100 fibers |
|---|---|---|
| Normal hair | 19.62 +/− 11.57 | 401.0 +/− 199.0 |
| Bleached hair | 5.78 +/− 1.94 | 222.0 +/− 91.2 |
| Bleached hair after 12 heat cycles with: | | |
| water | 5.76 +/− 1.94 | 238.0 +/− 93.1 |
| 1.2% D-Glucose | 5.56 +/− 1.16 | 187.0 +/− 74.8 |
| 1.0% D-Xylose | 9.74 +/− 2.13 | 432.0 +/− 137.0 |
| Bleached/permed hair | 6.28 +/− 1.95 | 88.3 + 34.4 |
| Bleached/permed hair after 12 heat cycles with: | | |
| water | 4.73 +/− 0.87 | 105.0 +/− 37.1 |
| 1.2% D-Glucose | 4.96 +/− 0.32 | 155.0 +/− 47.5 |
| 1.0% D-Xylose | 9.78 +/− 1.48 | 199.0 +/− 74.2 |

Example 5

Thermal Protection after 12 Cycles at 130° C.: C-3-C5 Monosaccharides (Triose, Tetrose and Pentose)

Normal blonde hair was subjected to 12 heat cycles, as described in Example 2, using the following treatment solutions: 0.1% D-Xylose (pentose), 0.1% D-Erythrose (tetrose), and 0.1% D-Glyceraldehyde (triose). Each of the C3 to C5 monosaccharides was effective in protecting or reducing the damage to the α-structure of the hair, as compared to water treatment (Table 15).

TABLE 15

Thermal Protection of Normal Blonde Hair with 0.1 wt % Solutions of C3-C5 Monosaccharides: 12 Heat Cycles at 130° C.

| Treatment | Doublet Peak Area, J/g hair |
|---|---|
| Normal blonde hairs, no treatment After 12 cycles at 130° C. | 13.51 +/− 4.06 |
| deionized water | 8.48 +/− 1.09 |
| 0.1% D-Xylose | 12.74 +/− 2.32 |
| 0.1% D-Erythrose | 13.20 +/− 7.15 |
| 0.1% D-Glyceraldehyde | 13.47 +/− 3.03 |

Example 6

Thermal Protection after 12 Cycles at 130° C. Using a Pentose Derivative (0.1 wt % D-Lyxosylimine)

Normal blonde hair was subjected to 12 heat cycles, as described in Example 2, using 0.1 wt % of the pentose amine derivative, D-Lyxosylimine in deionized water. The lyxosylimine solution protected the α-structure hair, as compared to water treatment (Table 16).

TABLE 16

Thermal Protection of Normal Blonde Hair with 0.1 wt % Lyxosylimine: 12 Heat Cycles at 130° C.

| Treatment | Doublet Peak Area, J/g hair |
|---|---|
| Normal blonde hair, no treatment After 12 cycles at 130° C.: | 13.51 +/− 4.06 |
| deionized water | 8.48 +/− 1.09 |
| 0.1% D-Lyxosylimine | 11.49 +/− 3.56 |

Example 7

Protection of Bleached Hair against Protein Loss in Water with D-Xylose and Oligomers (XyloBiose Syrup, and Xylo-Oligo 95P)

Bleached hair is known to lose protein in water to a greater degree, as compared to normal hair. Sandhu and Robbins, *J. Soc. Cosmet. Chem.*, 44, 163-175 (1993). This protein loss in water represents additional damage to the hair that occurs when the hair is washed. D-xylose and some xylose-based raw materials help prevent this protein loss from bleached hair in water.

XyloBiose Syrup is a raw material that contains about 15 wt % of xylobiose (dimer) and about 12 wt % of xylose. Xylo-Oligo 95P is a raw material containing about 22 wt % of xylobiose. Bleached hair was rinsed and blot-dried with a paper-towel. The treatment solution was then applied to the hair for 10 min at 45° C., and the hair was blow-dried. The procedure was repeated 5 times. Each of the following solutions was tested:
1% D-Xylose
1% Xylo-Oligo 95P
1.5% XyloBiose Syrup
deionized water-control treatment Following blow drying, a hair swatch (0.5 g) was immersed in 25 mL of deionized water for 1 h at 45° C. and the water was analyzed for the protein content. Id. As shown in Table 17, treatment with a xylose-based solution protected the hair, resulting in a decrease in the protein loss from the bleached hair, as compared to the control treatment, i.e., water.

TABLE 17

Protein Loss from Bleached Hair in Water: Effect of Treatment

| Treatment | Protein loss, microgram/g hair |
|---|---|
| Water treatment | 275.7 +/− 95.8 |
| 1% Xylose | 200.9 +/− 36.5 |
| 1% Xylo-Oligo 95P | 179.8 +/− 19.2 |
| 1.5% Xylo-Biose Syrup | 174.6 +/− 6.8 |

Example 8

Protection of Relaxed Kinky Hair with Xylose Solutions

Straightening of kinky or curly hair using alkaline formulas (pH 13-14) is a well-established practice. These formulas are highly efficient in straightening the hair, but cause damage to the hair due to the high pH.

Kinky hair was relaxed using 2.5% sodium hydroxide (20 min at room temperature). The hair was thoroughly rinsed with water, and a treatment solution was applied for 10 min at 45° C. Each of the following treatment solutions were tested: a) 1% D-xylose, b) 5% D-xylose, and c) deionized water-control treatment.

The cuticle loss was estimated as follows. The relaxed/treated hair (0.5 g) was immersed in 2.5 mL deionized water for 15 min at 45° C. The hair was removed and UV transmittance of the remaining cloudy suspension was determined. The greater the transmittance, the less material is suspended, and therefore, the less damage to the hair.

As shown in Table 18, the xylose-treated hair was protected, i.e., demonstrated a greater degree of preservation of the α-structure and the tensile strength, and less cuticle loss as compared to water treatment.

TABLE 18

Effect of Xylose Treatment on Relaxed Ethnic Hair

| Treatment | Double Peak Area*, J/g hair | Work to Break J/m² | Transmittance, at 600 nm |
|---|---|---|---|
| Water (control) | 6.55 +/− 1.32 | 741 +/− 174 | 0.8545 |
| 1% D-Xylose | 14.10 +/− 2.52 | 749 +/− 151 | 0.9545 |
| 5% D-Xylose | 21.35 +/− 19.02 | 1,200 +/− 222 | 0.9339 |

*The double peak area for the normal ethnic hair, J/g hair = 18.33 +/− 6.92

Example 9

Repairing Hair Following Extrinsic Damage using Pentoses

It is known that when bleached hair is stretched in water, its extension to break is significantly greater than that of the normal hair, indicating damage to the hair fiber. However, when bleached and bleached/permed hair is treated with 1% D-xylose prior to heat application, the extension to break was significantly shorter, as compared to the non-treated or water-treated hair (Table 19) indicating that the damaged hair fiber is repaired by the application of a xylose solution and heating. The corresponding DSC data for the bleached and bleached/permed hair, as well as the wet tensile strength (Work 25%) are presented in Example 4, Table 14.

The repairing of the damaged hair by pentoses is further supported by changes in the hair chemical composition that are observed when the hair was treated with pentose solutions, followed by heat application. Specifically, the amounts of lysine and arginine decreased, as compared to the hair treated with water (Table 19). The change in the lysine/arginine content, in conjunction with the decreased extension to break, appears to indicate that some cross-linking processes occur when the hair is heated in the presence of pentoses.

TABLE 19

Chemical Composition and Extension to Break in Bleached and Bleached/Permed Hair: Effect of 12 Cycles at 130° C.

| Treatment | Dia-Stron, wet fibers Extension, %, n = 100 | Lysine wt % | Arginine wt % |
|---|---|---|---|
| Normal hair | 57.60 +/− 10.20 | 3.0 +/− 0.1 | 9.1 +/− 0.1 |
| Bleached hair | 64.40 +/− 8.22 | 2.9 +/− 0.1 | 9.0 +/− 0.1 |
| Bleached hair after 12 cycles at 130° C. with: | | | |
| water | 58.60 +/− 7.33 | 2.7 +/− 0.1 | 8.7 +/− 0.1 |
| 1.0% D-Xylose | 52.80 +/− 9.29 | 1.9 +/ 0.1 | 8.0 +/− 0.1 |
| Bleached/permed hair | 65.50 +/− 7.55 | 2.9 +/− 0.1 | 9.2 +/− 0.1 |
| Bleached/permed hair after 12 cycles at 130° C. with: | | | |
| water | 62.00 +/− 6.15 | 2.7 +/− 0.1 | 9.1 +/− 0.1 |
| 1.0% D-Xylose | 54.30 +/− 4.70 | 1.6 +/− 0.1 | 7.2 +/− 0.1 |

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method of protecting a keratinous fiber from extrinsic damage comprising
    applying to said keratinous fiber, in an amount sufficient to protect said keratinous fiber, a composition comprising xylose or a derivative thereof;
    wherein said xylose or a derivative thereof is present in said composition at a concentration ranging from 0.01% to 5.00% relative to the total weight of the composition,
    wherein said protected keratinous fiber has a dry tensile strength of at least about 950 J/m²;
    wherein said protected keratinous fiber has a wet tensile strength of at least about 275 J/m²; and
    wherein said protected keratinous fiber has a alpha structure of at least about 7.5 J/g.

2. The method according to claim 1, wherein said composition further comprises at least one additional sugar, said at least one additional sugar being different than said xylose or a derivative thereof.

3. The method according to claim 2, wherein said at least one additional sugar is chosen from monosaccharides, disaccharides, and polysaccharides.

4. The method according to claim 3, wherein said monosaccharides are chosen from hexoses.

5. The method according to claim 4, wherein said hexoses are chosen from allose, altrose, glucose, mannose, gulose, idose, galactose, talose, sorbose, psicose, fructose, and tagatose.

6. The method according to claim 2, wherein said at least one additional sugar is present in said composition at a concentration ranging from 0.01% to 5.00% relative to the total weight of the composition.

7. The method according to claim 1, wherein said composition is in the form of a liquid, oil, paste, stick, dispersion, emulsion, lotion, gel, or cream.

8. The method according to claim 1, wherein said keratinous fiber is chosen from hair, eyelashes, and eyebrows.

9. The method according to claim 1, wherein said extrinsic damage is caused by heating, UV radiation, or chemical treatment.

10. The method according to claim 1, wherein said composition protects a keratinous fiber from extrinsic damages and repairs a keratinous fiber following extrinsic damage.

* * * * *